United States Patent
Shang et al.

(10) Patent No.: US 12,100,201 B2
(45) Date of Patent: Sep. 24, 2024

(54) MULTI-MODAL AQUATIC BIOMASS ESTIMATION

(71) Applicant: Aquabyte, Inc., San Francisco, CA (US)

(72) Inventors: Bryton Shang, San Francisco, CA (US); Alok Saxena, San Francisco, CA (US)

(73) Assignee: Aquabyte, Inc., San Francisco, CA (US)

( * ) Notice: Subject to any disclaimer, the term of this patent is extended or adjusted under 35 U.S.C. 154(b) by 377 days.

(21) Appl. No.: 17/678,848

(22) Filed: Feb. 23, 2022

(65) Prior Publication Data
US 2023/0267731 A1 Aug. 24, 2023

(51) Int. Cl.
*G06K 9/00* (2022.01)
*G01N 33/12* (2006.01)
(Continued)

(52) U.S. Cl.
CPC ............. *G06V 20/05* (2022.01); *G01N 33/12* (2013.01); *G01S 15/96* (2013.01); *G06T 7/70* (2017.01); *G06V 10/764* (2022.01); *G06T 2207/10016* (2013.01); *G06T 2207/30242* (2013.01); *G06V 2201/07* (2022.01)

(58) Field of Classification Search
CPC .......... G06T 2207/30242; A01K 61/95; A01K 61/60
See application file for complete search history.

(56) References Cited

U.S. PATENT DOCUMENTS 11,089,762 B1 8/2021 Kozachenok et al.
2013/0284105 A1* 10/2013 Han .................. A01K 61/60
119/230
(Continued)

FOREIGN PATENT DOCUMENTS

WO WO-2019232247 A1 * 12/2019 ............. A01K 61/13

OTHER PUBLICATIONS

International Search Report and Written Opinion, PCT App. No. PCT/US2023/013151, Jul. 25, 2023, 14 pages.

*Primary Examiner* — Hadi Akhavannik
(74) *Attorney, Agent, or Firm* — NICHOLSON DE VOS WEBSTER & ELLIOTT LLP (57) ABSTRACT

Computer-implemented techniques for multi-modal aquatic biomass estimation includes determining a fish mass measurement, a fish count, or a direct fish biomass estimate from a sample of one or more digital images or digital video captured by a digital camera immersed underwater in a fish farm enclosure. A technique further includes determining a plurality of fish densities for a plurality of water volumes within the fish farm enclosure based on analysis of signals received from a plurality of bias estimation sensors immersed underwater in the fish farm enclosure. The technique also includes computing a bias-adjusted fish mass measurement, fish count, or direct fish biomass estimate for the fish farm enclosure based on (i) the fish mass measurement, the fish count, or the direct fish biomass estimate determined from the sample of one or more digital images or digital video captured by the digital camera immersed underwater in the fish farm enclosure and (ii) the plurality of fish densities determined for the plurality of water volumes.

20 Claims, 4 Drawing Sheets

(51) Int. Cl.
    *G01S 15/96*     (2006.01)
    *G06T 7/70*     (2017.01)
    *G06V 10/764*     (2022.01)
    *G06V 20/05*     (2022.01)

(56) References Cited

U.S. PATENT DOCUMENTS

| | | | |
|---|---|---|---|
| 2017/0245480 A1* | 8/2017 | Hakonarson | A01K 61/95 |
| 2020/0267947 A1* | 8/2020 | Krossli | A01K 61/95 |
| 2021/0076645 A1* | 3/2021 | Hakonarson | A01K 61/90 |
| 2021/0209351 A1 | 7/2021 | Young et al. | |
| 2022/0279765 A1* | 9/2022 | Stone | A01K 61/10 |

* cited by examiner

MULTI-MODAL AQUATIC BIOMASS ESTIMATION

BACKGROUND

The disclosed subject matter relates to computer-implemented techniques for multi-modal aquatic biomass estimation.

Aquaculture is the farming of aquatic organisms (e.g., fish) in both coastal and inland areas involving interventions in the rearing process to enhance production. Aquaculture has experienced dramatic growth in recent years. The United Nations Food and Agriculture Organization has estimated that aquaculture accounts for at least half of the world's fish that is used for food.

The rise of aquaculture has fostered interest in techniques that improve the production processes in fish farms. Along the same lines, there is interest in fish biomass estimation techniques that can help fish farmers optimize feeding, control stocking densities, and determine the optimal time to harvest.

Traditional techniques to estimate fish biomass involve manual sampling and weighing, which is often invasive, time consuming, and labor-intensive. Thus, less invasive, more efficient, and more cost-effective techniques are desired.

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

BRIEF DESCRIPTION OF DRAWINGS

Various embodiments in accordance with the present disclosure will be described with reference to the drawings, in which.

DETAILED DESCRIPTION

The disclosed techniques for multi-modal aquatic biomass estimation encompass a method implementation, a non-transitory storage medium implementation, and a computer system implementation.

In one implementation of the disclosed techniques, the method for multi-modal aquatic biomass estimation is performed by one or more computing devices. The performance of the method by the one or more computing devices includes the step of determining a fish mass measurement, a fish count, or a direct fish biomass estimate from a sample of one or more digital images or digital video captured by a digital camera immersed underwater in a fish farm enclosure. The method further includes the step of determining a plurality of fish densities for a plurality of water volumes within the fish farm enclosure based on analysis of signals received from a plurality of bias estimation sensors immersed underwater in the fish farm enclosure. The method also includes the step of computing a bias-adjusted fish mass measurement, fish count, or direct fish biomass estimate for the fish farm enclosure based on (i) the fish mass measurement, the fish count, or the direct fish biomass estimate determined from the sample of one or more digital images or digital video captured by the digital camera immersed underwater in the fish farm enclosure and (ii) the plurality of fish densities determined for the plurality of water volumes.

In one implementation of the disclosed techniques, the non-transitory storage medium for multi-modal aquatic biomass estimation stores instructions which, when executed by one or more computing devices, cause the one or more computing devices to perform the above method for multi-modal aquatic biomass estimation.

In one implementation of the disclosed techniques, the computer system for multi-modal aquatic biomass estimation includes one or more hardware processors, storage media, and instructions stored in the storage media which, when executed by the one or more hardware processors, cause the one or more hardware processors to perform the above-method for multi-modal aquatic biomass estimation.

These and other implementations, as well as the disclosed techniques generally, are described in greater detail below with reference to drawings.

The disclosed techniques for multi-modal aquatic biomass estimation include using a computer vision-based fish biomass estimation system ("biomass estimation system"), a bias estimation system, and an extrapolation system. While the biomass estimation system, the bias estimation system, and the extrapolation system are described and depicted variously herein as being implemented using the same computer system (e.g., the same one or more computing devices), there is no requirement that this be the case. Instead, each can be implemented using a separate computer system.

Figure 1:
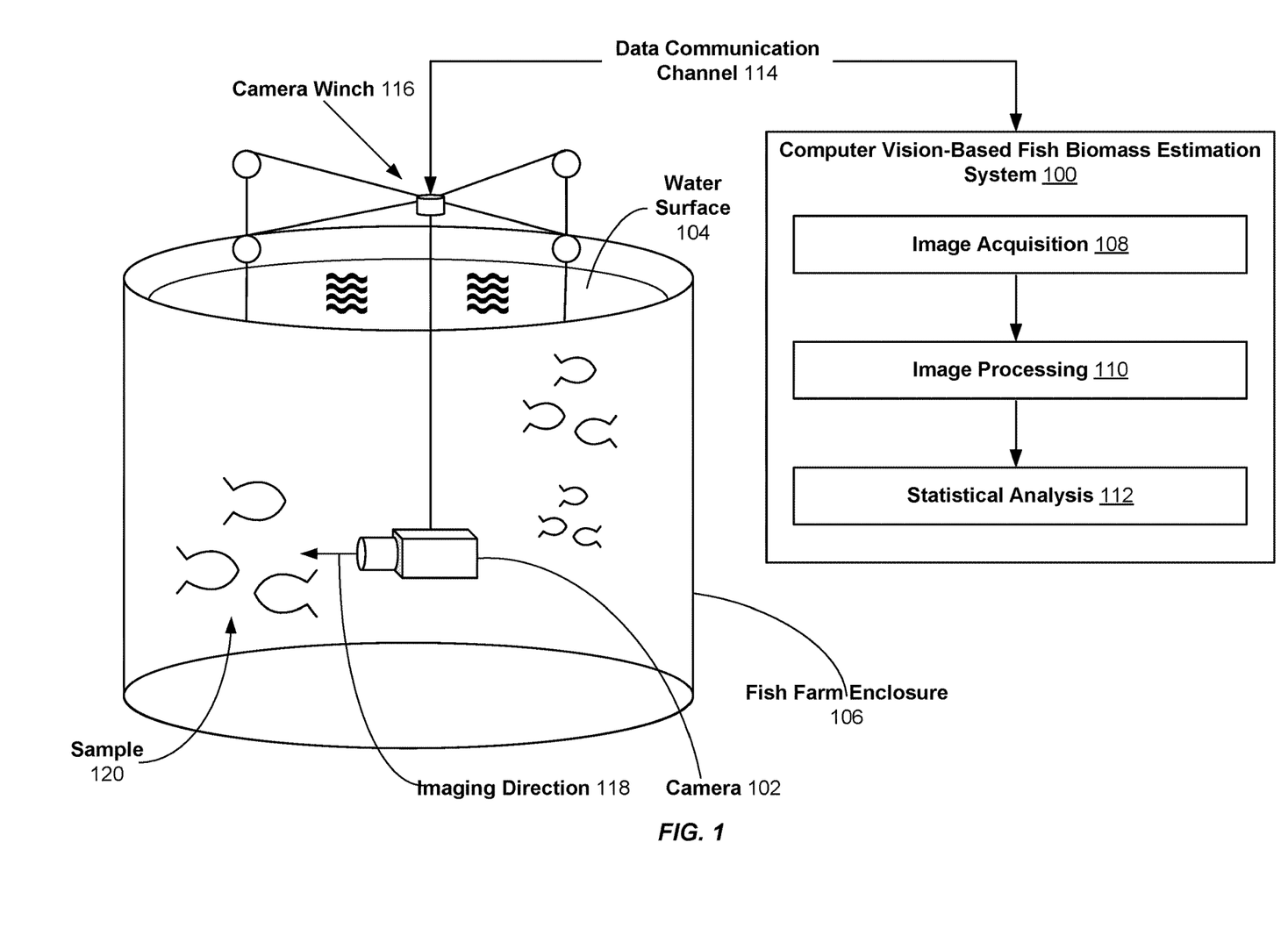
FIG. 1 depicts a computer vision-based aquatic biomass estimation system according to some embodiments.

FIG. 1 depicts a computer vision-based aquatic biomass estimation system 100. A monocular or stereo vision camera 102 is immersed under the water surface 104 in a fish farm enclosure 106. Camera 102 uses visible light to capture images or video of fish swimming freely in enclosure 106. The captured images or video provide pixel information from which quantitative information is extracted and analyzed for object recognition.

No type or configuration of camera 102 is required. In a possible implementation, camera 102 is an approximately 12-megapixel color or monochrome camera with a resolution of approximately 4096 pixels by 3000 pixels, and a frame rate of 1 to 8 frames per second. Although different cameras with different capabilities can be used according to the requirements of the implementation at hand. The lens or lenses or camera 102 can be selected based on an appropriate baseline and focal length to capture images of fish swimming in front of camera 102 in enclosure 106 where fish are close enough to the lens(es) for proper pixel resolution and feature detection in the captured image, but far enough away from the lens or lenses such that the fish can fit entirely in the image or video frame. For example, an 8-millimeter focal length lens with high line pair count (lp/mm) can be used such that the pixels can be resolved. The baseline of camera 102 can have greater variance such as, for example, within the range of 6 to 12-millimeter baseline.

Enclosure 106 can be framed by a plastic or steel cage that provides a substantially conical, cubic, cylindrical, spherical, or hemispherical shape. Enclosure 106 can hold several fish of a particular type (e.g., Atlantic salmon) depending on various factors such as the size of enclosure 106 and the maximum stocking density of the particular fish. For example, an enclosure 106 for Atlantic salmon can be 50 meters in diameter, 20-50 meters deep, and hold up to approximately 200,000 salmon assuming a maximum stocking density of 10 to 25 kg/m3. While enclosure 106 can be a net pen or sea-cage located in the open sea or open water, enclosure 106 can be a fish farm pond, tank, or other fish farm enclosure.

Camera 102 can be attached to winch system 116. Winch 116 allows camera 102 to be relocated underwater in enclosure 106. This allows camera 102 to capture images or video of fish from different locations within enclosure 106. For example, winch 116 can allow camera 102 to move around the perimeter of enclosure 106 and at various depths within enclosure 106. Winch 116 system can also allow control of pan and tilt of camera 102. Winch 116 can be operated manually by a human controller such as, for example, by directing user input to a winch control system located above water surface 104.

Winch 116 can operate autonomously according to a winch control program configured to adjust the location of camera 102 within enclosure 106. The autonomous winch control system can adjust the location of camera 102 according to a series of predefined or pre-programmed adjustments or according to detected signals in enclosure 102 that indicate better or more optimal locations within enclosure 106 for capturing images or video of fish relative a current position or orientation of camera 102. A variety of signals can be used such as, for example, machine learning and computer visions techniques applied to images or video captured by camera 102 to detect schools or clusters of fish currently distant from camera 102 such that a location that is closer to the school or cluster can be determined and the location, tilt, or pan of camera 102 adjusted to capture more suitable images of the fish. The same techniques can be used to automatically determine that camera 102 should remain or linger in a current location or orientation because camera 102 is currently in a good position to capture suitable images of fish. Instead of using winch 116 to position camera 102 within enclosure 106, the housing of camera 102 can include underwater propulsion mechanisms such as propellers or water jets. In this case, camera 102 can move within enclosure 106 autonomously as in a self-driving fashion. Also in this case, camera 102 can include components and software to control autonomous navigation such as underwater LiDAR and computer vision-software.

While camera 102 can operate using natural light (sunlight), an ambient lighting apparatus can be attached to camera 102 or otherwise located within enclosure 106. For example, the light apparatus can illuminate a volume of water in front of camera 102 lens(es) with ambient lighting in the blue-green spectrum (450 nanometers to 570 nanometers). This spectrum can be used to increase the length of the daily sample period during which useful images of fish in enclosure 106 can be captured. For example, depending on the current season (e.g., winter), time of day (e.g., sunrise or sunset), and latitude of enclosure 106, only a few hours during the middle of the day can be suitable for capturing useful images without using ambient lighting. This daily period can be extended with ambient lighting. Use of fluorescent, LED, or other artificial lighting is also possible.

Although not shown in FIG. 1, a mechanical feed system that is connected by physical pipes to enclosure 106 can be present in the aquaculture environment. The feed system can deliver food pellets via the pipes in doses to the fish in enclosure 106. The feed system can include other components such as a feed blower connected to an air cooler which is connected to an air controller and a feed dose-r which is connected to a feed selector that is connected to the pipes to enclosure 106. The fish biomass estimates generated according to the disclosed techniques can be used as input to the feed system for determining the correct amount of feed in terms of dosage amounts and dosage frequency, thereby improving the operation of the feed system.

As well as being useful for determining the correct amount of feed, the fish biomass estimates generated according to the disclosed techniques are also useful for determining more optimal feed formulation. Feed formulation includes determining the ratio of fat, protein, and other nutrients in the food pellets fed to the fish in enclosure 106. Using accurate biomass estimates generated by the disclosed techniques for fish in a particular enclosure, precise feed formulations for the fish in that enclosure can be determined. In this way, it is also possible to have different formulations for the fish in different enclosures based on the different biomass estimates determined by the disclosed techniques for those enclosures.

In addition to being useful for feed dosage optimization and feed formulation optimization, the accurate biomass estimates generated according to the disclosed techniques are also useful for determining optimal harvest times and maximizing sale profit for fish farmers. For example, fish farmers can use the biomass estimates to determine how much of different fish sizes they can harvest and bring to market. For example, the different fish sizes can be distinguished in the market by 1-kilogram increments. Thus, accurate biomass estimates are important to fish farmers to accurately determine which market bucket (e.g., the 4 kg to 5 kg bucket, the 5 kg to 6 kg bucket, etc.) the fish in enclosure 106 belong to. Having accurate biomass estimates also improves fish farmers' relationships downstream in the market such as with slaughterhouse operators and fish futures markets. Along the same lines, an accurate fish biomass estimate is useful for compliance with governmental regulations. For example, in Norway, a salmon farming license can impose a metric ton limit. Biomass estimates generated according to the disclosed techniques can be useful for ensuring compliance with such licenses.

System 100 includes various functional modules including image acquisition 108, image processing 110, and statistical analysis 112. Digital images or video captured by camera 102 are sent via data communication channel 114 to system 100. Data communication channel 114 can be a wired or wireless data communication channel. For example, data communication channel 114 can be a wired fiber data communication channel or a wireless data communication channel such as one based on a wireless data communication standard such as, for example, a satellite data communication standard or a standard in the IEEE 802.11 family of wireless standards.

It is also possible for system 100 to be a component of camera 102. In this case, data communication channel 114 is not needed to connect camera 102 to system 100. Instead, data communication channel 114 can be used to connect camera 102 to another system (not shown) that processes the results produced by system 100.

Regardless of if data communication channel 114 is used to convey images, video, or results produced by system 100, the results produced by system 100 can be provided to another system such as, for example, a web application system that provides a web browser-based or a mobile phone-based graphical user interface at client computing devices. The graphical user interface can visually present the results produced by system 100 or information derived therefrom such as in a web dashboard or the like. The results produced by system 100 or the information derived therefrom presented in the graphical user interface can include a measurement of the mass of fish in enclosure 106 ("fish mass measurement"), a count of fish in enclosure 106 ("fish count"), or a direct estimate of the biomass of fish in enclosure 106 ("direct fish biomass estimate").

Image acquisition 108 includes receiving the images or video captured by camera 102 and storing the images or video on a storage media (e.g., storage media of system 100) for further processing by image processing 110 and statistical analysis 112. Image acquisition 108 can perform some basic filtering of images or video such as discarding unusable images or video such as, for example, images or video frames that do not appear to contain any aquatic organisms or are of poor quality because of inadequate lighting or because camera 102 was in motion when the images or video was captured resulting in blurry images or video.

Image acquisition 108 can also perform cataloging of the images and video captured by camera 102. Cataloging can include associating captured images or video with metadata reflecting the situation or environment in enclosure 106 in which or at the time the images or video were captured by camera 102. Image acquisition 108 can associate captured images or video with metadata in storage media (e.g., storage media of system 100). Such metadata can include, but is not limited to, dates and times of when associated images or video were captured by camera 102 and position information for camera 102 when associated images or video were captured. The dates and times can be provided by a clock either of camera 102 or system 100. The position information can be provided by a global positioning satellite sensor affixed to camera 102, provided by camera winch system 116, or provided by an accelerator sensor of camera 102 such as, for example, a microelectromechanical system sensor (MEMS).

However provided, the position information can indicate the position of camera 102 underwater in enclosure 106 in one or more spatial dimensions. The position information can indicate the position of camera 102 in the volume of water within enclosure 106. For example, the position information can indicate one or more coordinates in a first plane and a coordinate in a second plane that is perpendicular to the first plane. For example, the first plane can be parallel to water surface 104. The position information, then, can indicate an x-axis coordinate and a y-axis coordinate in the first plane and a z-axis coordinate in the second plane. For example, the x-axis coordinate, and the y-axis coordinate can correspond to the position of camera 102 at water surface 104 and the z-axis coordinate can correspond to the depth of camera 102 underwater at the position of camera 102 at water surface 104 corresponding to the x-axis coordinate and the y-axis coordinate. In this example, the position of camera 102 within enclosure 106 is controllable by camera winch 116 in all three dimensions x, y, and z. However, camera winch 116 can allow positioning of camera 102 within enclosure 106 in just one or two of those dimensions. In this case, the dimension or dimensions that are not controllable by winch 116 can be fixed or otherwise predetermined.

The position information can also indicate the imaging orientation of camera 102 within enclosure 106. In particular, the position information can indicate the direction of the lens of camera 102 when images or video associated with the position information were captured. For example, the position information can indicate a compass heading or an angular position. Here, the compass heading or angular position can be with respect to a plane parallel with the imaging direction of the lens where the imaging direction of the lens is perpendicular to the plane of the lens. For example, in system 100, imaging direction 118 of lens of camera 102 is depicted as substantially parallel to water surface 104. However, imaging direction 118 of lens of camera 102 can instead be substantially perpendicular to water surface 104 such as, for example, if camera 102 is positioned nearer to the bottom of enclosure 106 and imaging direction 118 is towards water surface 104 or if camera 102 is positioned nearer to water surface 104 and imaging direction 118 is towards the bottom of enclosure 106.

The position information can also indicate a pitch angle of imaging direction 118 relative to a plane parallel to water surface 104 or relative to a plane perpendicular to water surface 104. For example, the pitch angle of imaging direction 118 as depicted in FIG. 1 can be zero degrees relative to a plane parallel to water surface 104 or ninety degrees relative to a plane perpendicular to water surface 104. Depending on the pitch of image direction 118, the pitch angle can range between −90 degrees and +90 degrees or equivalently between 0 and 180 degrees.

Reference herein to the "position" of camera 102 can encompass any one of the following or a combination two or more thereof: an x-axis position of camera 102, a y-axis position of camera 102, a z-axis position of camera 102, a compass heading of imaging direction 118 of camera 102, an angular position of imaging direction 118 of camera 102, a pitch angle of imaging direction 118 of camera 102, a longitudinal position of camera 102, a latitudinal position of camera 102, an elevation of camera 102, or a underwater depth of camera 102.

The volumetric size of enclosure 106 and the number of fish in enclosure 106 can be such that, at a given position in enclosure 106, camera 102 cannot capture sufficiently high-quality images or video of all the fish in enclosure 106 for use by system 100 to accurately estimate a fish mass measurement, a fish count, or a direct fish biomass estimate of all of the fish in enclosure 106. Characteristics of the lens or lenses of camera 102 and the particular requirements of the imaging application at hand such as focal length, aperture, maximum aperture, and depth of field can limit the volume of water within enclosure 106 of which camera 102 at a given position can capture sufficiently high-quality images or video. As a result, the images or video captured by camera 102 at a given position can be only a sample 120 of all fish in enclosure 106. As used herein, a "sample" as in, for example, sample 120, refers to one or more images or video of one or more fish in enclosure 106 captured by camera 102 and processed by system 100 to estimate a fish mass measurement, a fish count, or a direct fish biomass estimate of the one or more fish.

Sample 120 may not be representative of the entire fish population in enclosure 106. In other words, sample 120 can have a bias. The bias can be severe. Severe bias can cause substantial overestimation or underestimation when sample 120 is used by system 100 to estimate a fish mass measurement, a fish count, or a direct fish biomass estimate of all fish in enclosure 106. Various situational and environment conditions in enclosure 104 can contribute to the bias of sample 120 ("sampling bias"). Such conditions can include the position of camera 102 when sample 120 is captured and the location and spatial distribution of fish within the enclosure 104 when sample 120 is captured.

To attempt to reduce bias, sample 120 can be captured when the fish in enclosure 106 are being fed. This tends to reduce the spatial distribution of the fish population in enclosure 106 as the fish tend to congregate around where the feed is being dispensed into enclosure 106 by a mechanical feed dispenser above, below, or at water surface 104. Even so, sample 120 captured at feeding time can still have significant bias. For example, sample 120 can include mostly larger more powerful fish that are able to push out the smaller weaker fish from the area in the enclosure 106 where the feed is being dispensed, or sample 120 can omit fish that are satiated or sick or otherwise not feeding at the time.

For fish mass measurement, statistical analysis 112 can use a polynomial, linear, power curve, or other mathematical model for computing a fish weight (mass) of a target fish based on one or more fish size parameters for the target fish. Image processing 110 can identify the target fish in sample 120. For example, image processing 110 can use machine learning-aided image segmentation to identify portions of images or video frames that contain an image of a fish. In some implementations, image processing 110 incorporates a deep convolutional neural network to aid in segmentation of target fish from sample 120. Image processing 120 can then use two-dimensional (2D) or three-dimensional (3D) image processing techniques to determine from sample 120 the one or more fish size parameters of the target fish for input to the model. A fish size parameter can include an estimated length, area, width, or perimeter of the target fish. The model can be target fish species-specific and can incorporate a bend model to account for a bend of the target fish in sample 120 in case the body of the target fish is not straight in sample 120. Multiple fish mass measurements of multiple target fish identified in sample 120 can be determined.

Various computer vision techniques can be employed by image processing 110 to obtain a fish count of sample 120. Such computer vision techniques can include one or more of the following methods: neural network, data fitting, area counting, curve evolution, fish localization, image thinning, connected component, or object tracking.

For direct fish biomass estimation, statistical analysis 112 can compute a weight (mass) of a target fish directly by its volume and its density (mass=volume×density). The density of the target fish can be predetermined such as by the particular species of the target fish. The volume of the target fish can be determined by image processing 110 from sample 120 using various techniques including computer vision technology such as 2D or 3D image processing techniques aided by deep learning such as a convolutional neural network. The computer vision techniques can be aided by laser scanning technology. For example, a LiDAR suitable for underwater use can be affixed to camera 102 for laser scanning fish in imaging direction 118. For example, a laser scanner in combination with a monocular camera 102 can be used. The laser scanner projects structural light onto the fish and 2D or 3D cartesian coordinates of the fish's surface can be determined based on sample 120 by image processing 110 to represent the fish's shape.

An overall fish mass measurement, fish count, or direct fish biomass estimate for sample 120 can be determined by statistical analysis 112 as an average, mean, or probability distribution of individual corresponding determinations.

As mentioned, sample 120 can be biased. Thus, a simple extrapolation method to compute the overall fish mass measurement, fish count, or direct fish biomass estimate for entire enclosure 106 such as by using a fixed multiple applied to sample 120 can result in substantial overestimation or underestimation. To correct for the bias of sample 120, the disclosed techniques use a bias estimation system. Generally speaking, the bias estimation system obtains data from multiple sensors located underwater in enclosure 106. The sensors are positioned to sample different volumes of water within enclosure 106 including the volume from which sample 120 was captured. The sensor data provides an estimate of the density of fish in each water volume at a time corresponding to when sample 120 was captured by camera 102. The extrapolation system computes an overall bias-adjusted fish mass measurement, fish count, or direct fish biomass estimate for entire enclosure 106 based on the fish mass measurement, fish count, or direct fish biomass estimate for sample 120 and the densities determined from the active acoustics sensor data.

Figure 2:
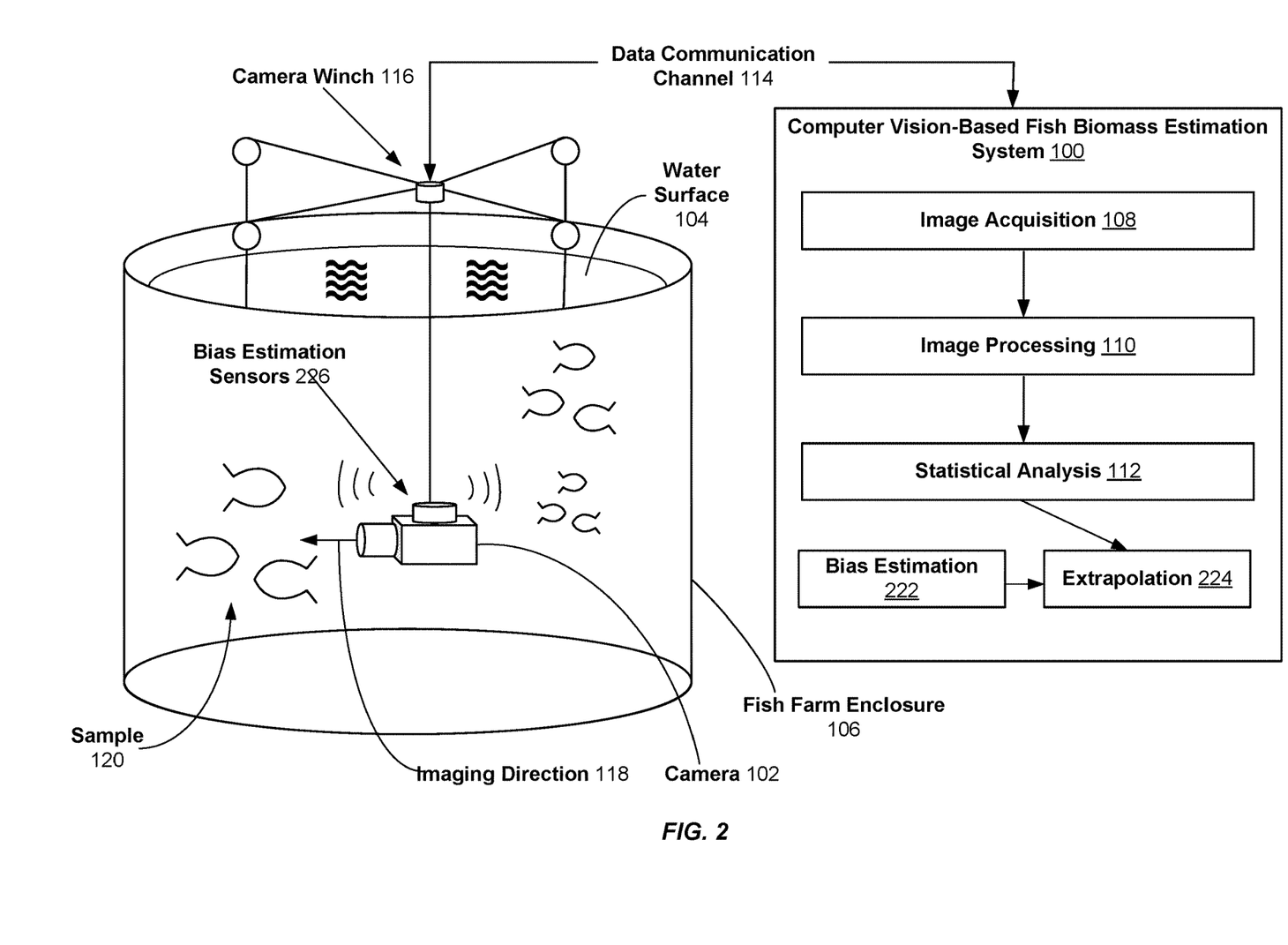
FIG. 2 depicts the computer vision-based aquatic biomass estimation system of FIG. 1 with the addition of a bias estimation system according to some embodiments.

FIG. 2 depicts the computer vision-based aquatic biomass estimation system of FIG. 1 with the addition of a bias estimation system. Bias estimation system encompasses bias estimation sensors 226, bias estimation functionality 222, and extrapolation functionality 224. Bias estimation sensors 226 is sometimes referred to herein as bias estimation sensor array 226.

In an implementation, bias estimation sensors 226 are active acoustics sensors. The active acoustics sensors emit sound waves in different directions within enclosure 106 at a certain frequency or set of frequencies to remotely detect fish in enclosure 106. An active acoustic sensor can be an echosounder or other fish finding transducer, for example.

An echosounder can have a transducer that emits acoustic waves that propagate within a volume of water within enclosure 106. When the acoustic waves encounter fish in enclosure 106, the acoustic waves are reflected back toward the echosounder as an echo signal. Scattered echo signals received back at the transducer of the echosounder are converted into voltage parameters recorded for subsequent analysis. Several fish can be estimated based on the physical characteristic that the strength of the echo signal is proportional to the number of fish (fish density) in the water volume targeted by the echosounder (target water volume).

Split-beam technology can be used to measure the target strength of fish. An echosounder can project a beam of sound within enclosure 106. The center of the beam of sound can have more concentrated power. As such, a fish within or near the center of the acoustic beam can result in a strong echo signal. However, the same fish nearer to the edge of the acoustic beam can result in a relatively weaker echo signal. To avoid mistakenly interpreting the weaker echo signal returning from a fish near the edge of the acoustic beam as a smaller sized fish than if the same fish were nearer to the center of the acoustic beam, an echosounder can be configured with a transducer that emits multiple (e.g., three or more) acoustic beams instead of just a single acoustic beam. For example, an echosounder can emit four acoustic beams. By emitting multiple acoustic beams, the position of fish within the overall acoustic beam can be determined to compensate for the difference in echo signal intensity when the fish is nearer to the edge of the overall acoustic beam compared to closer to the center of the overall acoustic beam.

While an echo sounder can employ split-beam technology, it is not required in an implementation. Instead, an echosounder can emit a single acoustic beam such as, for example, an acoustic beam with a relatively wide cone angle.

When the fish density is low in the target water volume, an echo counting method can be used to measure fish density by dividing the fish number obtained directly from the echosounder by the volume of the target water volume. When the fish density is relatively high in the target water volume when fish are congregating and cannot be easily identified as single fish, an echo integration method can be used to estimate the number of fishes by dividing the integral value of the echo signal intensity of the fish shoal in the target water volume by the target strength of an individual fish. In either case, an estimate of the number of fish in the target water volume is obtained. More generally, an estimate of the fish density of the target water volume is obtained.

At least two and up to eight active acoustics sensors can be positioned underwater within enclosure 106. In the example of FIG. 2, bias estimation sensors 226 are affixed to the housing of camera 102 and are configured to emit acoustic waves in a plane parallel to imaging direction 118. For example, two, four, six, or eight bias estimation sensors 226 can be affixed to housing of camera 102, each positioned in different directions so as to cover different target water volumes within enclosure 106.

However, it is also possible for bias estimation sensors 226 to be positioned in a fixed position such as affixed to the cage of enclosure 106. For example, an active acoustics sensor can be positioned at the bottom of enclosure 106 and configured to emit acoustic waves toward water surface 104 or an active acoustics sensor can be positioned at the top of enclosure 106 configured to emit acoustic waves toward the bottom of enclosure 106. It is also possible for active acoustic sensors 226 be positioned along the perimeter of enclosure 106 and configured to emit acoustic waves toward the center of enclosure 106.

In any case, each bias estimation sensor 226 provides data and information by which bias estimation 222 can determine a fish density for a corresponding target bias estimation sensor water volume (target water volume) within enclosure 106. The fish density can be based on sensor data and information that is obtained from or determined by bias estimation sensors 226 at a time corresponding to when camera 102 captures sample 120. In this way, bias estimation sensors 226 provide a general estimate of the fish density in enclosure 106 at a time corresponding to when camera 102 captures sample 120. Bias estimation 222 can break this total estimate down by target water volume for each bias estimation sensor 226 to obtain a general model of the distribution of the fish density within enclosure 106. A fish density determined by bias estimation 222 based on data and information obtained from bias estimation sensors 226 can be a fish measurement, a fish count, or a direct fish biomass estimate.

The size and shape of the target water volume for each bias estimation sensor 226 can be based on a model of the water volume that the sensor is configured to scan which can depend on various such factors including environmental factors such as turbidity of the water within enclosure 106. The location of the target water volume within enclosure 106 can be based on the location of the corresponding bias estimation sensor 226 and its beam direction. If the sensor is affixed to the housing of camera 102, then the position of camera 102 when sample 120 is captured can be used to determine the location of the target water volume within enclosure 106 for the sensor. In any case, when camera 102 captures sample 120, bias estimation sensors 226 can provide data and information for a corresponding set of target water volumes within enclosure 106 from which a fish density can be estimated by bias estimation 222 for each target water volume. Bias estimation 222 can then determine the target water volume or volumes from which sample 120 was captured by camera 102 based on the position of camera 102 at the time sample 120 was captured and the positions of the target water volumes for the sensors 226 at the time sample 120 was captured.

Bias estimation 222 and extrapolation 224 can then compute a bias adjusted fish mass measurement, fish count, or direct fish biomass estimate for the entire enclosure 106. The bias adjusted fish mass measurement, fish count, or direct fish biomass estimate can be computed based on the fish mass measurement, fish count, or direct fish biomass estimate computed for sample 120 and the per-target water volume fish densities.

Generally speaking, a bias adjustment can be computed that reflects how representative the target water volume from which sample 120 was captured (the sample target water volume) is compared to the other target water volumes for the other active acoustics sensors 226. For example, the fish density for each target water volume can be compared to the total (sum) of all fish densities for all target water volumes for all bias estimation sensors 226 to obtain an estimate of the percentage of the total fish density in enclosure 106 at the time sample 120 was captured. These percentages can be then used to extrapolate the fish mass measurement, the fish count, or the direct fish biomass estimate for the entire enclosure 106 from the fish mass measurement, fish count, or direct fish biomass estimate computed for sample 120. For example, the extrapolated or bias adjusted fish mass measurement, the fish count, or the direct fish biomass estimate for the entire enclosure 106 can be computed as:

$$Xe = \Sigma_{i=1}^{n=2} Pi * Xs$$

Here, Xe represents the extrapolated or bias adjusted fish mass measurement, the fish count, or the direct fish biomass estimate for the entire enclosure 106. The parameter n represents the number of bias estimation sensors 226 and hence the number of target water volumes. For example, n can range between two and eight or more. The parameter Pi represents the percentage of the total fish density across all target water volumes that is allocated to target water volume i. The parameter Xs represents the fish mass measurement, fish count, or direct fish biomass estimate computed for sample 120.

Figure 3:
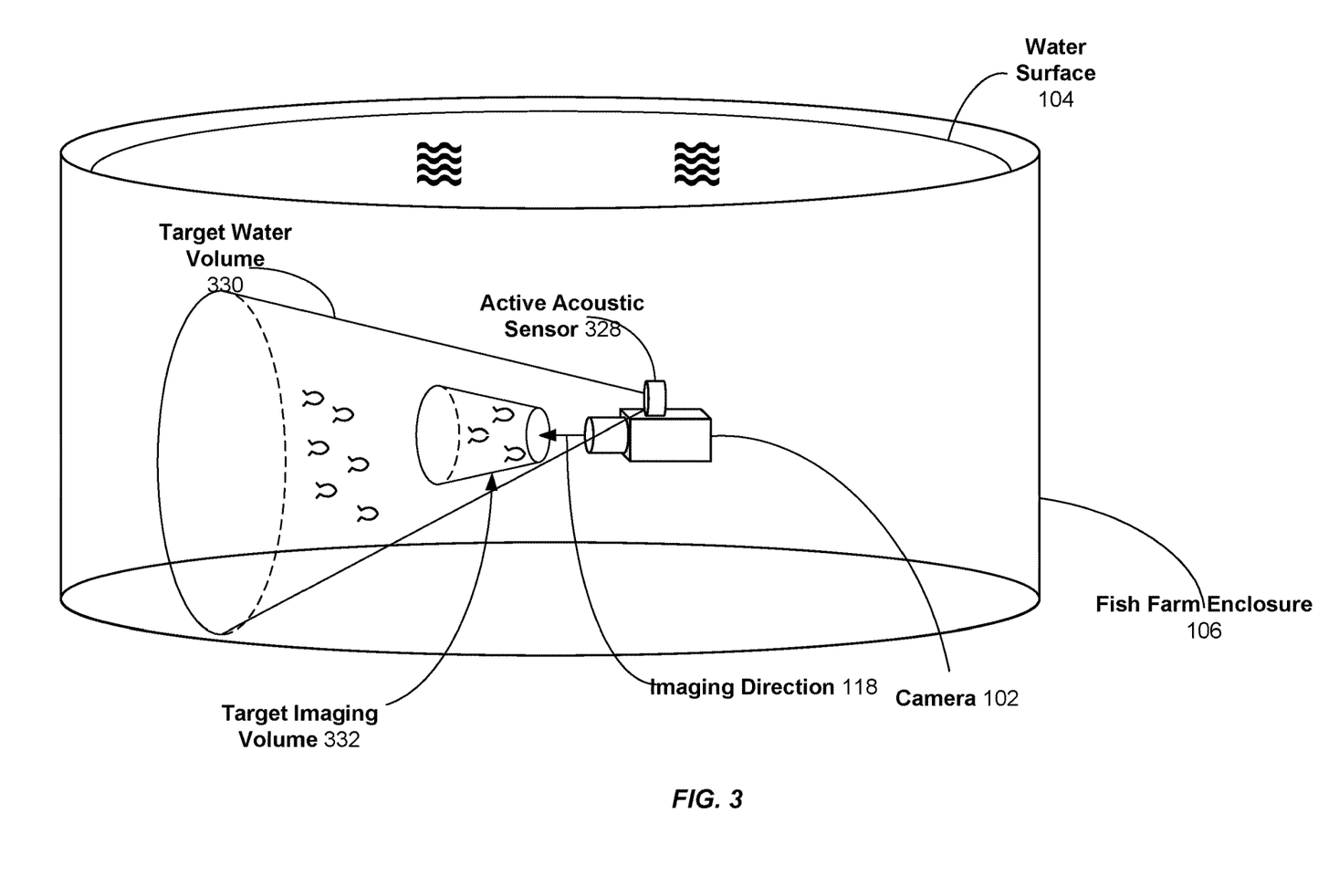
FIG. 3 depicts use of an active acoustic sensor for bias adjustment according to some embodiments.

FIG. 3 depicts use of an active acoustic sensor 328 for bias adjustment. In this example, active acoustic sensor 328 is affixed to the housing of camera 102. Sensor 208 is positioned on the housing of camera 102 to emit the center of its acoustic beam in the same general direction as imaging direction 118. The housing of camera 102 can be configured with additional active acoustic sensors but positioned to emit the center of their respective acoustic beams in different directions so as to provide greater directional coverage of enclosure 106. For example, camera 102 can be affixed with four active acoustic sensors with one positioned in the same direction as imaging direction 118, another positioned in the opposite direction as imaging direction 118, yet another positioned in a direction perpendicular to imaging direction 118, and finally another positioned in a direction opposite to the fore mentioned sensor positioning perpendicularly to imaging direction 118. As an alternative, camera 102 can include four additional active acoustic sensors each positioned to emit the center of its acoustic beam at approximately forty-five degrees between a different pair of active acoustic sensors in the prior example. The number of active acoustic sensors used in an implementation can vary depending on a variety of factors including cost and the maximum effective cone angle of each acoustic beam emitted from the sensors.

The maximum effective cone angle (swathe angle) of each acoustic beam emitted from the sensors can vary depending on whether the sensors are single-beam or use split-beam technology. For example, a single-beam active acoustic sensor can have an acoustic beam with a cone angle between two (2) and fifteen (15) degrees while a multi-beam or split-beam active acoustic sensor can have an overall acoustic beam with a cone angle (swathe angle) between one hundred and twenty (12) and one hundred and seventy (170) degrees.

It should be noted that when active acoustic sensor 328 is a multi-beam or split-beam sensor, sensor 328 can emit multiple beams at different frequencies, with different cone angles (different swath angles), and in different directions. In this case, unless the context clearly indicates otherwise, reference above and elsewhere herein to the center of the acoustic beam of sensor 328 encompasses to the center of the centermost acoustic beam emitted by sensor 320.

While in the example of FIG. 3, active acoustic sensor 328 is positioned to emit the center of its acoustic beam substantially parallel to a plane of imaging direction 118, sensor 328 can be positioned in the housing of camera 102 to emit the center of its acoustic beam at a positive or negative angle upward or downward from a plane of imaging direction 118. For example, sensor 328 (and the other active acoustic sensors affixed to the housing of camera 102) can be positioned to emit the center of its acoustic beam at an upward or downward angle between zero (0) and fifteen (15) degrees above or below a plane of imaging direction 118.

Camera 102 has a target imaging water volume 332 within which camera 102 can capture usable quality images or video of fish that freely swim within enclosure 106. Images or video of fish outside target imaging water volume 332 captured by camera 102 can be unusable by image processing 110 for determining a fish measurement, a fish count, or a direct fish biomass estimate of sample 120. For example, unable images or video frames can include out-of-focus fish or fish at too low a resolution that result because the fish is outside target imaging water volume 332 when imaged by camera 102.

The size and shape of target imaging water volume 332 can vary depending on a variety of characteristics of camera 102 and the application at hand including the desired working distance and depth of focus of camera 102 configuration. Further, size and shape of target imaging water volume 332 can change at times depending on the environmental conditions within enclosure 106 such as the water turbidity and ambient lighting.

Target water volume 330 represents the volume of water that can be effectively scanned by sensor 328. Typically, the size of target water volume 330 is greater than the size of target imaging water volume 332. While in FIG. 3 target imaging water volume 332 is depicted entirely within target water volume 330, this need not be the case and the volumes can only partially overlap in an implementation.

In an implementation, instead of bias estimation sensors 226 being active acoustic sensors such as echosounders, bias estimation sensors 226 are active electric field sensors. In such an implementation, a plurality of active electric field electrodes can be placed in enclosure 106 to set an active alternating polarity electric field within enclosure 106. The frequency of the alternating polarity can sweep over a range of frequencies. An object or objects, conductive or nonconductive, within a target water volume within the electric field can change the capacitance behavior in the target water volume in accordance with the size and the composition of the object(s). Sensor electrodes can be placed in the electric fields to detect the local capacitance signals. From the local capacitance signals, the amount of fish biomass within the target water volume can be determined by bias estimation 222. A bias estimation sensor 226 can also be the camera itself. In this scenario, computer vision techniques are applied by bias estimation 222 to video captured by the camera as the camera moves about underwater to determine amounts of fish biomass within various target water volumes.

In some embodiments, in addition to or instead of determine a bias-adjusted biomass estimate, a variance estimate is determined. Additionally, or alternatively, a bias-adjusted biomass estimate, or a variance estimate can be determined based on applying deep learning-based computer vision techniques to video captured by the camera immersed underwater in the net pen. Such techniques can be used to determine the orientation of fish in the video images and swimming direction and this information used to determine a bias-adjusted biomass estimate or variance estimate.

Figure 4:
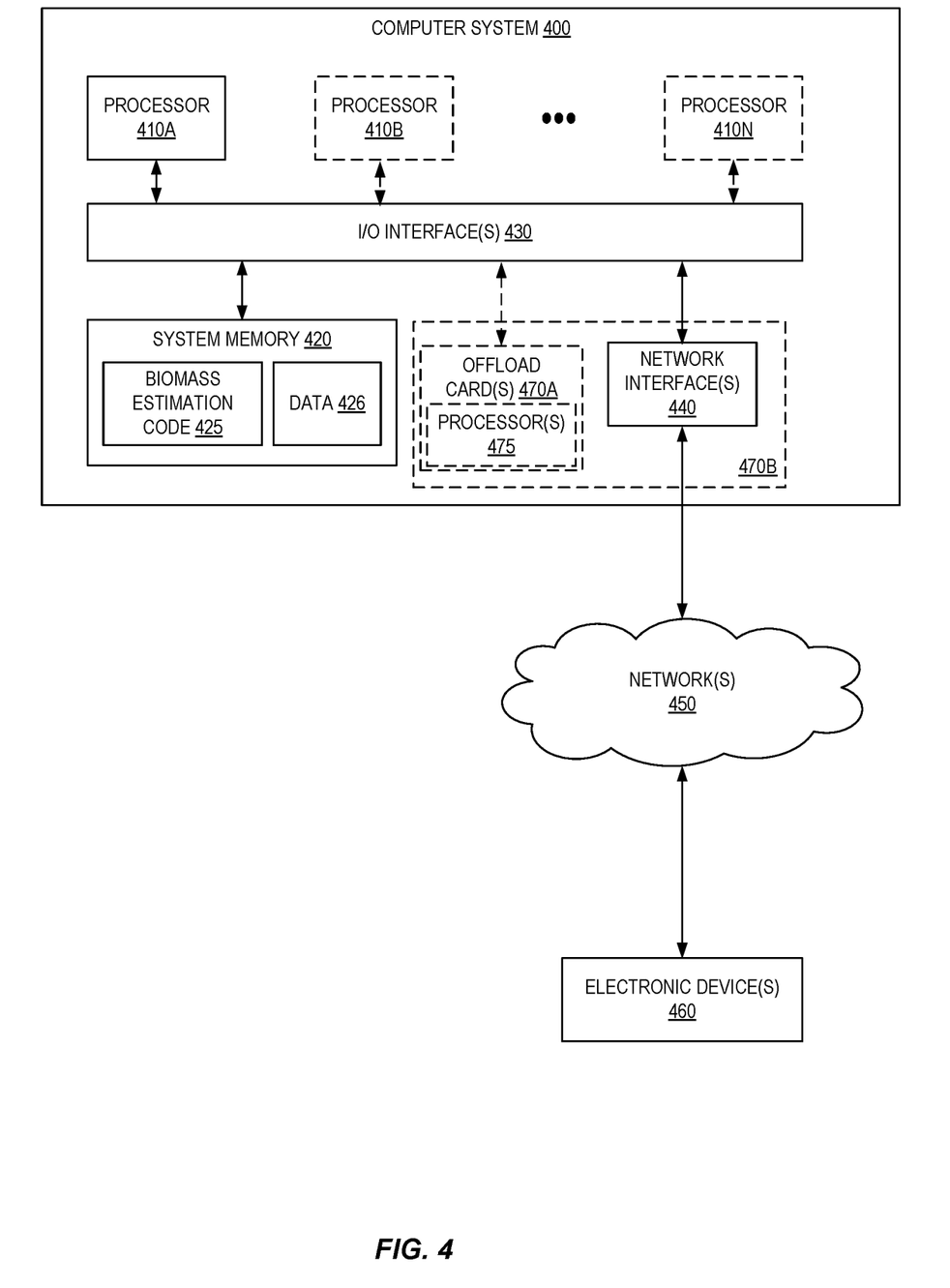
FIG. 4 is a block diagram illustrating an example computer system that can be used in some embodiments.

In some embodiments, a system that implements a portion or all of the techniques described herein can include a general-purpose computer system, such as the computer system 400 illustrated in FIG. 4, that includes, or is configured to access, one or more computer-accessible media. In the illustrated embodiment, the computer system 400 includes one or more processors 410 coupled to a system memory 420 via an input/output (I/O) interface 430. The computer system 400 further includes a network interface 440 coupled to the I/O interface 430. While FIG. 4 shows the computer system 400 as a single computing device, in various embodiments the computer system 400 can include one computing device or any number of computing devices configured to work together as a single computer system 400.

In various embodiments, the computer system 400 can be a uniprocessor system including one processor 410, or a multiprocessor system including several processors 410 (e.g., two, four, eight, or another suitable number). The processor(s) 410 can be any suitable processor(s) capable of executing instructions. For example, in various embodiments, the processor(s) 410 can be general-purpose or embedded processors implementing any of a variety of instruction set architectures (ISAs), such as the x86, ARM, PowerPC, SPARC, or MIPS ISAs, or any other suitable ISA. In multiprocessor systems, each of the processors 410 can commonly, but not necessarily, implement the same ISA.

The system memory 420 can store instructions and data accessible by the processor(s) 410. In various embodiments, the system memory 420 can be implemented using any suitable memory technology, such as random-access memory (RAM), static RAM (SRAM), synchronous dynamic RAM (SDRAM), nonvolatile/Flash-type memory, or any other type of memory. In the illustrated embodiment, program instructions and data implementing one or more desired functions, such as those methods, techniques, and data described above, are shown stored within the system memory 420 as biomass estimation code 425 (e.g., executable to implement, in whole or in part, to implement the biomass estimation techniques disclosed herein) and data 426.

In some embodiments, the I/O interface 430 can be configured to coordinate I/O traffic between the processor 410, the system memory 420, and any peripheral devices in the device, including the network interface 440 and/or other peripheral interfaces (not shown). In some embodiments, the I/O interface 430 can perform any necessary protocol, timing, or other data transformations to convert data signals from one component (e.g., the system memory 420) into a format suitable for use by another component (e.g., the processor 410). In some embodiments, the I/O interface 430 can include support for devices attached through various types of peripheral buses, such as a variant of the Peripheral Component Interconnect (PCI) bus standard or the Universal Serial Bus (USB) standard, for example. In some embodiments, the function of the I/O interface 430 can be split into two or more separate components, such as a north bridge and a south bridge, for example. Also, in some embodiments, some or all of the functionality of the I/O interface 430, such as an interface to the system memory 420, can be incorporated directly into the processor 410.

The network interface 440 can be configured to allow data to be exchanged between the computer system 400 and other devices 460 attached to a network or networks 450, such as other computer systems or devices as illustrated other figures, for example. In various embodiments, the network interface 440 can support communication via any suitable wired or wireless general data networks, such as types of Ethernet network, for example. Additionally, the network interface 440 can support communication via telecommunications/telephony networks, such as analog voice networks or digital fiber communications networks, via storage area networks (SANs), such as Fibre Channel SANs, and/or via any other suitable type of network and/or protocol.

In some embodiments, the computer system 400 includes one or more offload cards 470A or 470B (including one or more processors 475, and possibly including the one or more network interfaces 440) that are connected using the I/O interface 430 (e.g., a bus implementing a version of the Peripheral Component Interconnect-Express (PCI-E) standard, or another interconnect such as a QuickPath interconnect (QPI) or UltraPath interconnect (UPI)). For example, in some embodiments the computer system 400 can act as a host electronic device (e.g., operating as part of a hardware virtualization service) that hosts compute resources such as compute instances, and the one or more offload cards 470A or 470B execute a virtualization manager that can manage compute instances that execute on the host electronic device. As an example, in some embodiments the offload card(s) 470A or 470B can perform compute instance management operations, such as pausing and/or un-pausing compute instances, launching and/or terminating compute instances, performing memory transfer/copying operations, etc. These management operations can, in some embodiments, be performed by the offload card(s) 470A or 470B in coordination with a hypervisor (e.g., upon a request from a hypervisor) that is executed by the other processors 410A-310N of the computer system 400. However, in some embodiments the virtualization manager implemented by the offload card(s) 470A or 470B can accommodate requests from other entities (e.g., from compute instances themselves), and cannot coordinate with (or service) any separate hypervisor.

In some embodiments, the system memory 420 can be one embodiment of a computer-accessible medium configured to store program instructions and data as described above. However, in other embodiments, program instructions and/or data can be received, sent, or stored upon different types of computer-accessible media. Generally speaking, a computer-accessible medium can include any non-transitory storage media or memory media such as magnetic or optical media, e.g., disk or DVD/CD coupled to the computer system 400 via the I/O interface 430. A non-transitory computer-accessible storage medium can also include any volatile or non-volatile media such as RAM (e.g., SDRAM, double data rate (DDR) SDRAM, SRAM, etc.), read only memory (ROM), etc., that can be included in some embodiments of the computer system 400 as the system memory 420 or another type of memory. Further, a computer-accessible medium can include transmission media or signals such as electrical, electromagnetic, or digital signals, conveyed via a communication medium such as a network and/or a wireless link, such as can be implemented via the network interface 440.

Various embodiments discussed or suggested herein can be implemented in a wide variety of operating environments, which in some cases can include one or more user computers, computing devices, or processing devices which can be used to operate any of a number of applications. User or client devices can include any of a number of general-purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially available operating systems and other known applications for purposes such as development and database management. These devices also can include other electronic devices, such as dummy terminals, thin-clients, gaming systems, and/or other devices capable of communicating via a network.

Most embodiments use at least one network that would be familiar to those skilled in the art for supporting communications using any of a variety of widely-available protocols, such as Transmission Control Protocol/Internet Protocol (TCP/IP), File Transfer Protocol (FTP), Universal Plug and Play (UPnP), Network File System (NFS), Common Internet File System (CIFS), Extensible Messaging and Presence Protocol (XMPP), AppleTalk, etc. The network(s) can include, for example, a local area network (LAN), a wide-area network (WAN), a virtual private network (VPN), the Internet, an intranet, an extranet, a public switched telephone network (PSTN), an infrared network, a wireless network, and any combination thereof.

In embodiments using a web server, the web server can run any of a variety of server or mid-tier applications, including HTTP servers, File Transfer Protocol (FTP) servers, Common Gateway Interface (CGI) servers, data servers, Java servers, business application servers, etc. The server(s) also can be capable of executing programs or scripts in response requests from user devices, such as by executing one or more Web applications that can be implemented as one or more scripts or programs written in any programming language, such as Java®, C, C# or C++, or any scripting language, such as Perl, Python, PHP, or TCL, as well as combinations thereof. The server(s) can also include database servers, including without limitation those commercially available from Oracle®, Microsoft®, Sybase®, IBM®, etc. The database servers can be relational or non-relational (e.g., "NoSQL"), distributed or non-distributed, etc.

Environments disclosed herein can include a variety of data stores and other memory and storage media as discussed above. These can reside in a variety of locations, such as on a storage medium local to (and/or resident in) one or more of the computers or remote from any or all of the computers across the network. In a particular set of embodiments, the information can reside in a storage-area network (SAN) familiar to those skilled in the art. Similarly, any necessary files for performing the functions attributed to the computers, servers, or other network devices can be stored locally and/or remotely, as appropriate. Where a system includes computerized devices, each such device can include hardware elements that can be electrically coupled via a bus, the elements including, for example, at least one central processing unit (CPU), at least one input device (e.g., a mouse, keyboard, controller, touch screen, or keypad), and/or at least one output device (e.g., a display device, printer, or speaker). Such a system can also include one or more storage devices, such as disk drives, optical storage devices, and solid-state storage devices such as random-access memory (RAM) or read-only memory (ROM), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or web browser. It should be appreciated that alternate embodiments can have numerous variations from that described above. For example, customized hardware might also be used and/or particular elements might be implemented in hardware, software (including portable software, such as applets), or both. Further, connection to other computing devices such as network input/output devices can be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, Electrically Erasable Programmable Read-Only Memory (EEPROM), flash memory or other memory technology, Compact Disc-Read Only Memory (CD-ROM), Digital Versatile Disk (DVD) or other optical storage, magnetic cassettes, magnetic tape, magnetic disk storage or other magnetic storage devices, or any other medium which can be used to store the desired information and which can be accessed by a system device. Based on the disclosure and teachings provided herein, a person of ordinary skill in the art will appreciate other ways and/or methods to implement the various embodiments.

In the preceding description, various embodiments are described. For purposes of explanation, specific configurations and details are set forth to provide a thorough understanding of the embodiments. However, it will also be apparent to one skilled in the art that the embodiments can be practiced without the specific details. Furthermore, well-known features can be omitted or simplified in order not to obscure the embodiment being described.

Bracketed text and blocks with dashed borders (e.g., large dashes, small dashes, dot-dash, and dots) are used herein to illustrate optional operations that add additional features to some embodiments. However, such notation should not be taken to mean that these are the only options or optional operations, or that blocks with solid borders are not optional in certain embodiments.

Unless the context clearly indicates otherwise, the term "or" is used in the foregoing specification and in the appended claims in its inclusive sense (and not in its exclusive sense) so that when used, for example, to connect a list of elements, the term "or" means one, some, or all of the elements in the list.

Unless the context clearly indicates otherwise, the terms "comprising," "including," "having," "based on," "encompassing," and the like, are used in the foregoing specification and in the appended claims in an open-ended fashion, and do not exclude additional elements, features, acts, or operations.

Unless the context clearly indicates otherwise, conjunctive language such as the phrase "at least one of X, Y, and Z," is to be understood to convey that an item, term, etc. can be either X, Y, or Z, or a combination thereof. Thus, such conjunctive language is not intended to require by default implication that at least one of X, at least one of Y, and at least one of Z to each be present.

Unless the context clearly indicates otherwise, as used in the foregoing detailed description and in the appended claims, the singular forms "a," "an," and "the" are intended to include the plural forms as well.

Unless the context clearly indicates otherwise, in the foregoing detailed description and in the appended claims, although the terms first, second, etc. are, in some instances, used herein to describe various elements, these elements should not be limited by these terms. These terms are only used to distinguish one element from another. For example, a first computing device could be termed a second computing device, and, similarly, a second computing device could be termed a first computing device. The first computing device and the second computing device are both computing devices, but they are not the same computing device.

In the foregoing specification, the techniques have been described with reference to numerous specific details that can vary from implementation to implementation. The specification and drawings are, accordingly, to be regarded in an illustrative rather than a restrictive sense.

What is claimed is:

1. A method for multi-modal aquatic biomass estimation, comprising:
    determining a fish mass measurement, a fish count, or a direct fish biomass estimate from a sample comprising one or more digital images or digital video captured by a digital camera immersed underwater in a fish farm enclosure;
    determining a fish density for a water volume within the fish farm enclosure based on an analysis of signals received from a bias estimation sensor immersed underwater in the fish farm enclosure; and
    computing a bias-adjusted fish mass measurement, fish count, or direct fish biomass estimate for the fish farm enclosure based on:
        (i) the fish mass measurement, the fish count, or the direct fish biomass estimate determined from the sample of one or more digital images or digital video captured by the digital camera immersed underwater in the fish farm enclosure, and
        (ii) the fish density determined for the water volume;
    wherein the method is performed by at least one computing device.

2. The method of claim 1, wherein the fish density for the water volume within the fish farm enclosure comprises a fish count for the water volume.

3. The method of claim 1, wherein the bias estimation sensor comprises an active acoustic sensor, and wherein the method further comprises:

determining the fish density for the water volume within the fish farm enclosure based on analysis of echo signals received from the active acoustic sensor.

4. The method of claim 1, wherein the bias estimation sensor comprises an active electric field sensor, and wherein the method further comprises:
determining the fish density for the water volume within the fish farm enclosure based on analysis of capacitance signals received from the active electric field sensor.

5. The method of claim 1, further comprising:
determining a particular water volume of a plurality of water volumes from which at least a portion of the sample of one or more digital images or digital video is captured by the digital camera immersed underwater in the fish farm enclosure;
determining a particular fish density of a plurality of fish densities determined for the particular water volume; and
computing the bias-adjusted fish mass measurement, fish count, or direct fish biomass estimate for the fish farm enclosure based on the particular fish density as a percentage of the plurality of fish densities.

6. The method of claim 1, wherein the bias estimation sensor is affixed to the digital camera, and wherein the method further comprises determining a particular water volume of a plurality of water volumes from which at least the portion of the sample of one or more digital images or digital video is captured by the digital camera immersed underwater in the fish farm enclosure based on a position of the digital camera in the fish farm enclosure at a time the sample of one or more digital images or digital video is captured by the digital camera.

7. The method of claim 1, wherein the bias estimation sensor is the digital camera, the signals received from the bias estimation sensor comprise digital video, and the analysis of the signals comprises applying deep learning computer vision techniques to the digital video to determine the fish density.

8. A method for multi-modal aquatic biomass estimation, comprising:
determining a fish mass measurement, a fish count, or a direct fish biomass estimate from a sample of one or more digital images or digital video captured by a digital camera immersed underwater in a fish farm enclosure;
determining a position of the digital camera in the fish farm enclosure at a time the sample of the one or more digital images or digital video is captured by the digital camera; and
computing a bias-adjusted fish mass measurement, fish count, or direct fish biomass estimate for the fish farm enclosure based on:
(i) the fish mass measurement, the fish count, or the direct fish biomass estimate determined from the sample of the one or more digital images or digital video captured by the digital camera immersed underwater in the fish farm enclosure, and
(ii) the position of the digital camera in the fish farm enclosure at the time the sample of the one or more digital images or digital video is captured by the digital camera.

9. The method of claim 8, further comprising:
determining a fish density for a water volume within the fish farm enclosure based on an analysis of signals received from a bias estimation sensor immersed underwater in the fish farm enclosure; and
computing the bias-adjusted fish mass measurement, fish count, or direct fish biomass estimate for the fish farm enclosure based on:
(iii) the fish density for the water volume.

10. The method of claim 9, wherein the fish density for the water volume within the fish farm enclosure comprises a fish count for the water volume.

11. The method of claim 9, wherein the bias estimation sensor comprises an active acoustic sensor, and wherein the method further comprises:
determining the fish density for the water volume within the fish farm enclosure based on analysis of echo signals received from the active acoustic sensor.

12. The method of claim 9, wherein the bias estimation sensor comprises an active electric field sensor, and wherein the method further comprises:
determining the fish density for the water volume within the fish farm enclosure based on analysis of capacitance signals received from the active electric field sensor.

13. The method of claim 9, wherein the bias estimation sensor is the digital camera, the signals received from the bias estimation sensor comprise digital video, and the analysis of the signals comprises applying deep learning computer vision techniques to the digital video to determine the fish density.

14. A method for multi-modal aquatic biomass estimation, comprising:
determining a fish mass measurement, a fish count, or a direct fish biomass estimate from a sample of one or more digital images or digital video captured by a digital camera immersed underwater in a fish farm enclosure;
determining a fish density for a water volume within the fish farm enclosure based on an analysis of signals received from a bias estimation sensor immersed underwater in the fish farm enclosure;
determining a position of the digital camera in the fish farm enclosure at a time the sample of the one or more digital images or digital video is captured by the digital camera; and
computing a bias-adjusted fish mass measurement, fish count, or direct fish biomass estimate for the fish farm enclosure based on:
(i) the fish mass measurement, the fish count, or the direct fish biomass estimate determined from the sample of the one or more digital images or digital video captured by the digital camera immersed underwater in the fish farm enclosure,
(ii) the fish density for the water volume, and
(iii) the position of the digital camera in the fish farm enclosure at the time the sample of the one or more digital images or digital video is captured by the digital camera.

15. The method of claim 14, wherein the fish density for the water volume within the fish farm enclosure comprises a fish count for the water volume.

16. The method of claim 14, wherein the bias estimation sensor comprises an active acoustic sensor, and wherein the method further comprises:
determining the fish density for the water volume within the fish farm enclosure based on analysis of echo signals received from the active acoustic sensor.

17. The method of claim 14, wherein the bias estimation sensor comprises an active electric field sensor, and wherein the method further comprises:

determining the fish density for the water volume within the fish farm enclosure based on analysis of capacitance signals received from the active electric field sensor.

18. The method of claim 14, further comprising:

determining a particular water volume of a plurality of water volumes from which at least a portion of the sample of one or more digital images or digital video is captured by the digital camera immersed underwater in the fish farm enclosure;

determining a particular fish density of a plurality of fish densities determined for the particular water volume; and computing the bias-adjusted fish mass measurement, fish count, or direct fish biomass estimate for the fish farm enclosure based on the particular fish density as a percentage of the plurality of fish densities.

19. The method of claim 14, wherein the bias estimation sensor is affixed to the digital camera, and wherein the method further comprises determining a particular water volume of a plurality of water volumes from which at least the portion of the sample of one or more digital images or digital video is captured by the digital camera immersed underwater in the fish farm enclosure based on the position of the digital camera in the fish farm enclosure at the time the sample of one or more digital images or digital video is captured by the digital camera.

20. The method of claim 14, wherein the bias estimation sensor is the digital camera, the signals received from the bias estimation sensor comprise digital video, and the analysis of the signals comprises applying deep learning computer vision techniques to the digital video to determine the fish density.

* * * * *